(12) United States Patent
Hoek et al.

(10) Patent No.: US 6,615,067 B2
(45) Date of Patent: Sep. 2, 2003

(54) METHOD AND DEVICE FOR MEASURING PHYSICAL CHARACTERISTICS IN A BODY

(75) Inventors: Bertil Hoek, Vasteras (SE); Lars Tenerz, Uppsala (SE); Leif Smith, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 90 days.

(21) Appl. No.: 09/811,778

(22) Filed: Mar. 20, 2001

(65) Prior Publication Data

US 2001/0051769 A1 Dec. 13, 2001

Related U.S. Application Data

(60) Provisional application No. 60/199,348, filed on Apr. 25, 2000.

(30) Foreign Application Priority Data

Mar. 21, 2000 (EP) ............................................. 00850049

(51) Int. Cl.[7] ................................................ A61B 5/04
(52) U.S. Cl. ........................ 600/381; 600/301; 600/372
(58) Field of Search ................................. 600/372, 373, 600/377, 381, 549, 561, 301

(56) References Cited

U.S. PATENT DOCUMENTS

| | | | | | |
|---|---|---|---|---|---|
| 3,590,322 | A | * | 6/1971 | Carr | 128/908 |
| 4,690,152 | A | * | 9/1987 | Juncosa | 600/381 |
| 4,741,334 | A | * | 5/1988 | Irnich | 366/253 |
| 5,188,983 | A | | 2/1993 | Guckel et al. | |
| 5,513,636 | A | * | 5/1996 | Palti | 600/348 |
| 5,542,915 | A | | 8/1996 | Edwards et al. | |
| 5,628,777 | A | | 5/1997 | Moberg et al. | |
| 5,701,895 | A | * | 12/1997 | Prutchi et al. | 128/899 |
| 5,908,385 | A | * | 6/1999 | Chechelski et al. | 600/374 |
| 6,106,486 | A | * | 8/2000 | Tenerz et al. | 600/585 |
| 6,447,448 | B1 | * | 9/2002 | Ishikawa et al. | 128/899 |

FOREIGN PATENT DOCUMENTS

| | | | |
|---|---|---|---|
| EP | 0925803 | 6/1999 | |
| EP | 1169976 A1 | * 1/2002 | A61B/18/14 |
| WO | WO 91/08706 | 6/1991 | |

OTHER PUBLICATIONS

Article—"A New Technique for Transmission of Signals from Implantable Transducers", vol. 45, No. 5, May 1998 (Derek P. Lindsey, et al.)—IEEE Transactions of Biomedical Engineering.

Article—"An Ultraminiature Solid–State Pressure Sensor for a Cardiovascular Catheter", Dec., 1988 (Hin–Leung Chau et al.)—IEEE Transactions on Electron Devices.

* cited by examiner

*Primary Examiner*—Lee Cohen
*Assistant Examiner*—Henry M. Johnson, III
(74) *Attorney, Agent, or Firm*—Foley & Lardner

(57) ABSTRACT

A guide wire for measuring physiological characteristics inside a body includes a sensor (14) for monitoring the physical variable and for forming an output signal characteristic for the value of the physical variable. The sensor is connected to a first electrical potential of an electronic unit (22) via an electrical wire (11) extending along the guide wire. An internal body electrode (17) is connected to the sensor (14) and is in contact with body fluids surrounding the sensor circuit. The guide wire (10) is inserted into a vessel of the body (25), and a second electrode (21) is applied near the internal body electrode, and the sensor circuit is powered by a second potential of the electronic unit (22) via a part of the body.

22 Claims, 5 Drawing Sheets

METHOD AND DEVICE FOR MEASURING PHYSICAL CHARACTERISTICS IN A BODY

The Applicants hereby claim the benefit of priority of U.S. Provisional Application No. 60/199,348, filed Apr. 25, 2000, and European Application 00860049.8, filed Mar. 21, 2000. The entire contents of both of these applications are incorporated herein by reference.

FIELD OF THE INVENTION

The present invention relates to a guide wire assembly for intravascular investigations.

TECHNICAL BACKGROUND

It is known to mount a sensor on a guide wire and to position the sensor via the guide wire in a body vessel in a living body to detect a physical parameter such as pressure or temperature. The sensor includes elements that are directly or indirectly sensitive to the parameter. For example, temperature could be measured by observing the resistance of a conductor having temperature sensitive resistance, or by observing the length of an element having a known temperature related elongation.

In order to monitor the state of the sensor inside the body some type of communication means is necessary. In some cases, means is also needed for providing power to the sensor and/or the communicating means.

Therefore, in order to power and communicate with the sensor a plurality of cables for transmitting measuring signals are connected to the sensor, and are routed along the guide wire to be passed out from the vessel to an external monitoring unit via a connector assembly. In addition, the guide wire is typically provided with a central metal wire (core wire) serving both as a support for the sensor and as a conductor of a ground potential.

However, the use of numerous cables requires that the core wire at least partly has to be replaced by a tubular section accommodating the cables. This section forms a weak part of the guide wire, and exhibits a risk for buckling during manipulation within the vessel as well as a risk for non-symmetrical behaviour.

Also, conventional guide wire assemblies exhibit a problem in that they require a very difficult manual assembling procedure. The extremely small components must be assembled under a microscope. This procedure is both tedious and labour intensive.

An improved guide wire, addressing some of these problems, is described in the European patent application EP 0 225 803. EP 0 925 803 describes a guide wire having generally tubular conductors being disposed concentrically around the core wire, thereby allowing a simplified manufacturing process. However, the manufacturing of such a guide wire is still comparatively time consuming and expensive. Such a guide wire further requires a complicated connector.

Therefore, there remains a need for a simplified guide wire assembly including a physical property sensor that is inexpensive, easily manufactured, and easy to manipulate.

SUMMARY OF THE INVENTION

It is the object of the present invention to provide a system for intravascular investigation of a physiological variable inside a living body including an easy-to-manufacture and easy-to-manipulate guide wire.

The invention reduces the number of electrical conduits necessary for a sensor guide wire, making the wire easy to manufacture and easy to use. The invention also contemplates a method for measuring physiological variables using the guide wire system.

A detailed description of the invention is given hereinafter. However, it should be understood that the detailed description and specific examples, while indicating preferred embodiments of the invention, are given by way of illustration only. From this detailed ii description various changes and modifications within the spirit and scope of the invention will become apparent to those skilled in the art.

BRIEF DESCRIPTION OF THE DRAWINGS

The present invention will become more fully understood from the detailed description given herein, including the accompanying drawings. The drawings are given by way of illustration only and must not be construed as limiting the present invention. The drawings illustrate aspects of the invention, wherein.

DETAILED DESCRIPTION OF EMBODIMENTS

Figure 1:
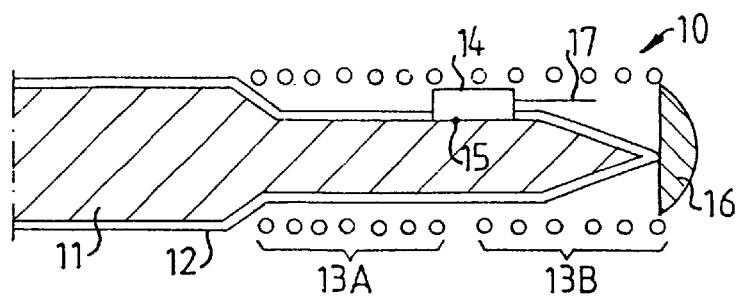
FIG. 1 is a cross sectional view of the distal end of a guide wire according to the invention.

First, a guide wire according to the present invention shall be described.

According to the invention, a sensor requiring electric energy for its operation is connected at the distal end of an insulated electrical wire. Also, an internal body electrode is connected directly to the sensor, or is connected to the sensor via an electronic circuit connected to the sensor. The internal body electrode is adapted to be disposed in contact with tissue of a living body, such as blood, when inserted into the body, i.e., it has a portion for direct contact with the body tissue when inserted into the patient.

In use, the sensor is inserted into a living body while the proximal end of the electrical wire is connected to a power source and the sensor and the internal body electrode is disposed at a site inside the body where measurements are to be made. Thus, the internal body electrode is placed in contact with the living body, and specifically in contact with body tissue such as the blood, in order to obtain electrical connection therewith.

In order to obtain a closed electrical circuit, a second electrode is connected to the power source and is brought to the vicinity of the internal body electrode. The second electrode has a portion for physical and electrical connection to patient, either directly or via a conductivity enhancing medium as is well in the art.

In one embodiment of the invention this is performed by placing the electrode on the skin of the patient, outside the site of measurement, in a manner similar to the application of an ECG electrode. In this embodiment, the electrical circuit is closed via the inner tissue and the skin of the patient.

In another embodiment of the invention the electrical circuit is closed by inserting the second electrode as well into the body in such a way that its distal end is placed near the site of measurement and is in contact with the body tissue of the patient. In this embodiment, the electrical circuit is closed internally via the tissue, i.e. typically the blood, of the patient.

It is possible to insert the sensor as well as the electrode or electrodes to any proper site within the body via a hollow tube, such as a suitable cannula or an introducer. In a preferred embodiment a sensor, an electronic circuit (if used), an internal body electrode, an electrical wire, and a second electrode (if used), are mounted on a guide wire structure. Such a structure is typically inserted via the femoral artery.

In a preferred embodiment, the electrical wire is integrated with the core wire of the guide wire. Using the core wire as the electrical wire reduces the number of components because a metal core wire extending axially through the guide wire is normally present in the guide wire anyway in order to provide proper stiffness to the guide wire. A guide wire having a core wire as the electrical wire will be used throughout this description for simplicity. However, it is clear that the method for communicating with the sensor described herein could be practiced with a separate electrical wire running along the guide wire, or running along another path.

The power source for use with the invention is an electronic unit situated outside of the patient's body. The electronic unit is capable of providing a suitable current through the electrical circuit partly involving the patient's body, as will be described below. In addition, the electronic unit is preferably provided with electronic circuits to interpret and present the output signal from the sensor circuit, as will be described below.

An embodiment of a guide wire of the present invention shall now be explained with reference to FIG. 1.

FIG. 1 shows a cross section of the distal end of a guide wire 10 according to the invention. A core wire 11, typically of stainless steel or a super-elastic alloy such as NITINOL® extends through the central axis of the guide wire. Core wire 11 is coated with an insulating layer 12, typically a polymer, such as Parylen®, silicone, Teflon®, polyimide, polyurethane, or a ceramic coating.

A proximal coil section 13A and a distal coil section 13B cover the distal end of the core wire. Proximal coil section 13A, which serves to provide the guide wire end with a smooth surface and a proper stiffness, is typically made of stainless steel. Distal coil section 13B is typically made from platinum. Distal section 13B is similar to proximal section 13A except that distal section 13B also provides x-ray opacity. Coils 13 provide a uniform outer diameter to the guide and facilitate the introduction of the guide wire into the artery. When inserted into an artery, coils 13 are penetrable by blood surrounding the guide wire end. The tip of the guide wire is closed by soldered arced tip 16.

It should be noted that the coil section arrangement is described to show the shape of the distal end of a typical guide wire as used presently. Other arrangements within the spirit and scope of the invention will occur to those skilled in the art.

A sensor 14 is attached to the core wire and is electrically connected thereto via a connection point 15. It should be understood that the sensor could include, in addition to a component sensitive to the physical property being measured, any electronic circuit necessary for its proper and useful function as a sensor as well as circuitry for superimposing a sensor output signal onto a carrier signal.

Circuitry for such superposition purposes is in itself well known to those skilled in the art. By way of example only, such circuitry may include devices such as voltage to frequency converters, analogue to digital converters, pulse width modulators and delta modulators.

Figure 11:
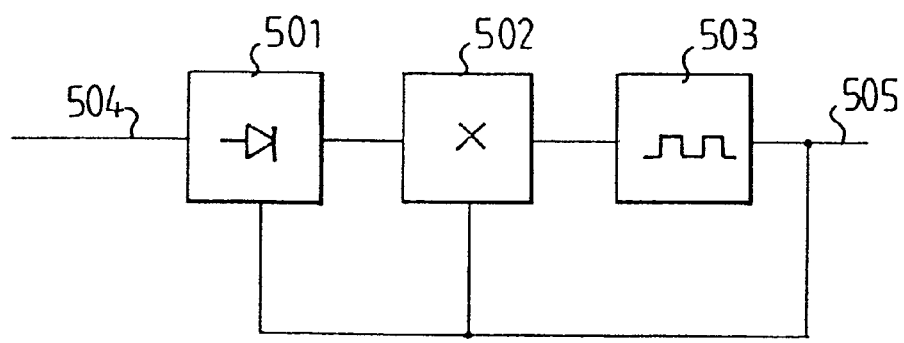
FIG. 11 is a block diagram showing an embodiment of a sensor and an associated circuitry.

An example of an embodiment of a sensor with an associated circuitry is shown in FIG. 11, comprising a rectifier 501, a sensor element 502 and a relaxation oscillator 503 connected in series. The input of rectifier 501 is connected to the guide wire core wire via a connection point 504. The output of relaxation oscillator 503 is connected to the internal body electrode via a connection point 505. Also, rectifier 501 and sensor element 502 are connected to the internal body electrode. The relaxation oscillator generates a square wave, i.e., the output signal flips from a minimum level to a maximum level (a digital "0" and a digital "1", respectively). The oscillating period or pulse width of such an oscillator, also known in the literature as an "astable multivibrator", can usually be controlled by a resistor-capacitor network characterized by one or several characteristic time constants RC, where R and C are resistance and capacitance values, respectively. Thus a resistive or capacitive sensor can be used to control the period time or pulse width of the oscillator.

Referring again to FIG. 1, the output signal from sensor 14 is transferred to the surrounding blood via an output signal electrode 17. Output signal electrode 17 is at least partially uninsulated and is at one end connected to sensor 14. Electrode 17 transfers the output from sensor circuit 14 via the surrounding blood between anyone of coil sections 13A, 13B. Because the core wire is insulated, the potential of the core wire does not interfere with electrode 17.

Figure 2:
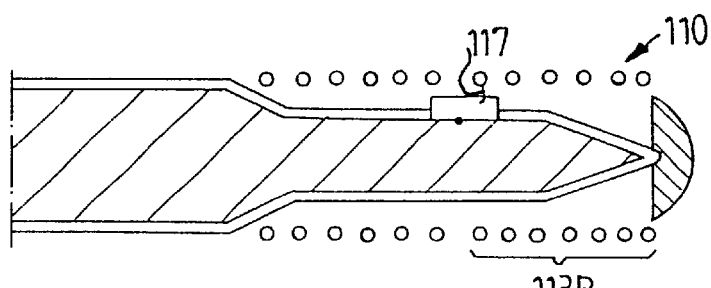
FIG. 2 is a cross sectional view of the distal end of a guide wire according to another embodiment of the invention.

An alternative embodiment of output signal electrode 117 is shown in FIG. 2, wherein components congruent to the components of FIG. 1 have similar numbering. According to FIG. 2, output signal electrode 117 is connected to, or forms a part of, one of coil sections 113B. While anyone of the coil sections are useful, at least a part of the selected section should not be insulated in order to allow contact with the surrounding body fluids. This alternative embodiment comprises a simple design that guarantees a proper contact with the surrounding parts of the body.

Figure 3:
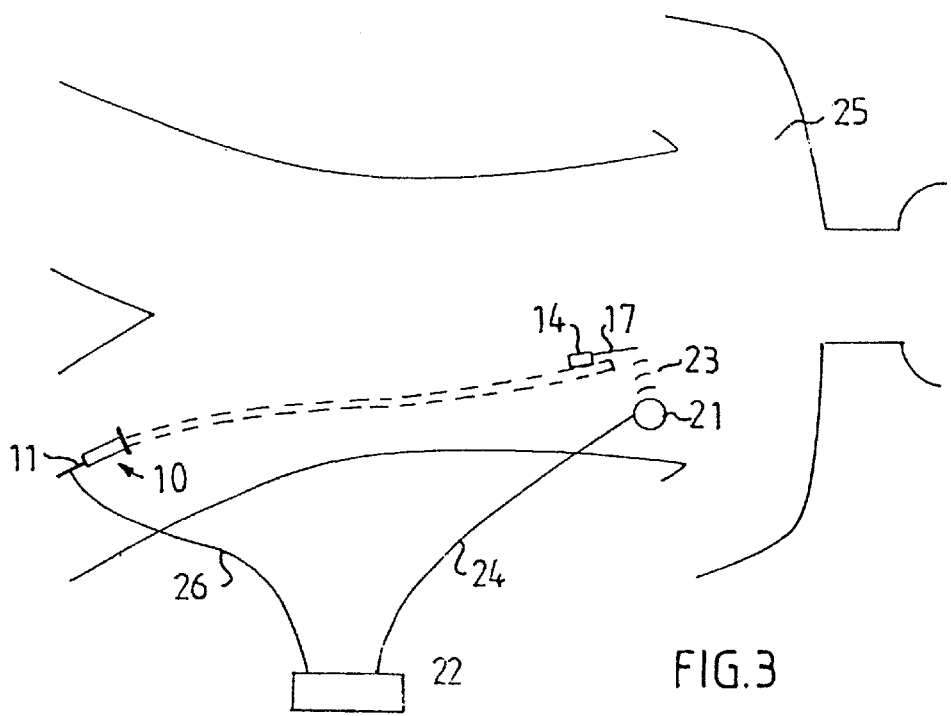
FIG. 3 is a schematic view illustrating a system according to the present invention used on a patient.

The use of a guide wire 19 according to the present invention, such as is illustrated in FIG. 1, is schematically shown in FIG. 3. Guide wire 10 is inserted into the femoral artery of a patient 25. The position of guide wire 10, sensor 14 and output signal electrode 17 inside the body is illustrated with dotted lines.

An external electrode 21, generally similar to an ECG electrode, is attached to the skin of patient 25 near the position for sensor circuit 14. External electrode 21 is coupled to an electronic unit 22 via an electrical wire 24. Guide wire 10, and more specifically core wire 11 thereof, is also coupled to electronic unit 22 via a wire 26 that is connected to core wire 11 using any suitable connector means (not shown), such as a crocodile clip-type connector or any other known connector.

Electronic unit 22 provides an electrical voltage to the circuit comprising wire 26, core wire 11 of the guide wire 10, sensor circuit 14, output signal electrode 17, blood and other patient tissue 23, electrode 21, and wire 24.

In use, sensor 14 is inserted into the patient, for example as has been described above with reference to FIG. 3, and an electrode 21 is applied approximately above output signal electrode 17, for example via the patient's skin as has also been described. The method to introduce the guide wire, as well as the method necessary to provide a proper electrically conducting attachment of the electrode applied to the skin of the patient, are well known to those skilled in the art. Core wire 11 and electrode 21 are connected to electronic unit 22.

The currents being generated through the patient's tissue due to the applied electric voltage have to be low enough to be safely transferred through the human body. Allowable values are preferably selected according to the international standard IEC 601-1 (1988), clause 19. Although a weak DC voltage could be used, it is preferred to use an AC voltage in order to obtain useful currents tough the body. By way of example, an alternating voltage with a frequency higher than 1 kHz makes it possible to allow currents up to 10 mA without risks for the health of the patient.

Figure 4:
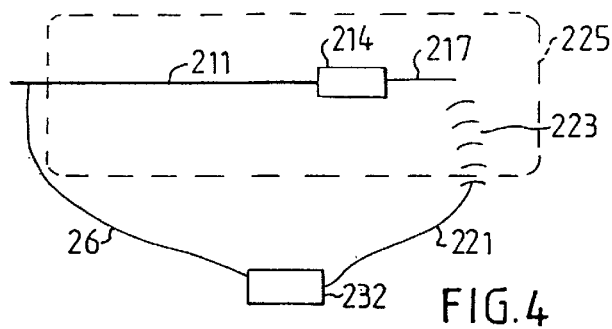
FIG. 4 is a schematic representation of a simple embodiment of the present invention

A very simple embodiment for measuring the temperature within a body corresponding to the description above is schematically shown in FIG. 4. The sensor is a temperature sensitive resistor 214, having a known relationship between temperature and resistance. One end of resistor 214 (corresponding to the connecting point 15 of FIG. 1) is connected to a core wire 211 and the other end is connected to an output signal electrode 217. The sensor is inserted into a body, schematically indicated as dotted line 223. An electronic unit 232 outside of the body provides a voltage to sensor 214 via a conduit 26, core wire 211, output signal electrode 217, body tissue 233, and an electrode 221 disposed on the skin of body 223.

The voltage provided by electronic unit 232 could be an AC or a DC voltage. Electronic unit 232 also includes means for registering the overall resistance of the circuit via the body. Such means are well known and will not be described herein. By measuring the overall resistance, and knowing the temperature-resistance relationship of the sensor, the temperature at the sensor is easily calculated.

The main advantage of this embodiment is simplicity. However, it has the drawback of low accuracy and reliability. These disadvantages are a result of influences from other resistances within the monitored circuit, for example the coupling impedance of skin electrode 221.

Generally, in the case of applying an AC voltage, the sensor is typically connected to a circuit that includes a rectifier that transforms the AC voltage to a DC voltage for driving the sensor selected to be sensitive to the physical parameter to be investigated. An example of a sensor for use in such an application and useful for measuring cardiovascular pressure, is described in Transducers '87 (The 4th international conference on solid state sensors and actuators), p. 344, "An ultraminiature solid-state pressure sensor for a cardiovascular catheter" by H. Chau and K. D. Wise.

As described above, the output signal of the sensor is processed by a circuit connected to the sensor in such a way that information representing the level of the monitored physical parameter is superimposed on the signal that is provided by the electronic unit.

Figure 5:
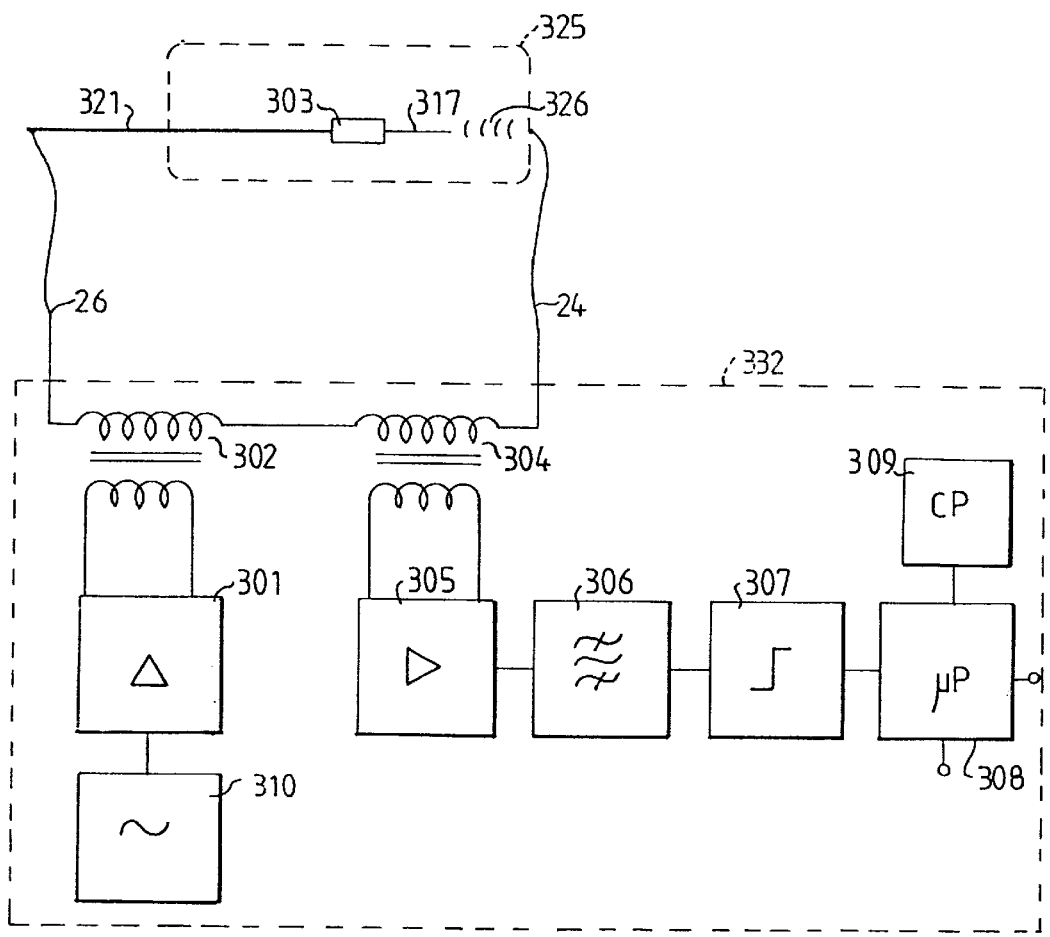
FIG. 5 is a block diagram of an embodiment of an electronic unit for use with the present invention.

The electronic unit includes circuitry to calculate the value of the investigated parameter based on the superimposed signal. An embodiment of such an electronic unit 332 is shown in FIG. 5. A guide wire assembly is schematically represented by a core wire 321, a sensor unit 303, and an internal body electrode 317 for providing an electrical signal via issue 326 of a patient. The guide wire assembly is introduced into patient 325. The electronic unit 332 is connected to core wire 321 via a cable 26, and to the outside of the body via the tissue and a second cable 24.

Electronic unit 332 comprises a drive oscillator 310, providing an AC voltage typically in the range of 2–10 V at a frequency in the range of 100 kHz–1 MHz, connected to a drive amplifier 301 which drives a first transformer 302. First transformer 302 is non-galvanically coupled to the circuit through the body, to provide a feeding voltage.

A second transformer 304, which is also coupled to the circuit through the body in a non-galvanic way, is used for detection of the superimposed signal. The signal is amplified with an amplifier 305, and a narrow band-pass filter 306 is used to eliminate low and high frequency interference. By way of example only, the band-pass filter could be a so called phase-sensitive amplifier or a synchronous amplifier.

A Schmitt-trigger (or comparator) 307 is connected to the output of band-pass filter 306, to trigger (send a digital "1") at a selected voltage threshold level. A digital microprocessor 308 correlates the trigger pulses with a clock pulse generator 309 to count the number of clock pulses between consecutive trigger pulses.

FIGS. 6A to 6E, which are interconnected with respect to a time axis, illustrate the decoding of a measure signal provided by sensor unit 303 in a set-up according to FIG. 5. Sensor unit 303 is a unit including an oscillator, corresponding to the sensor circuit described above with reference to FIG. 11.

Figures 6A, 6B, 6C, 6D, 6E:
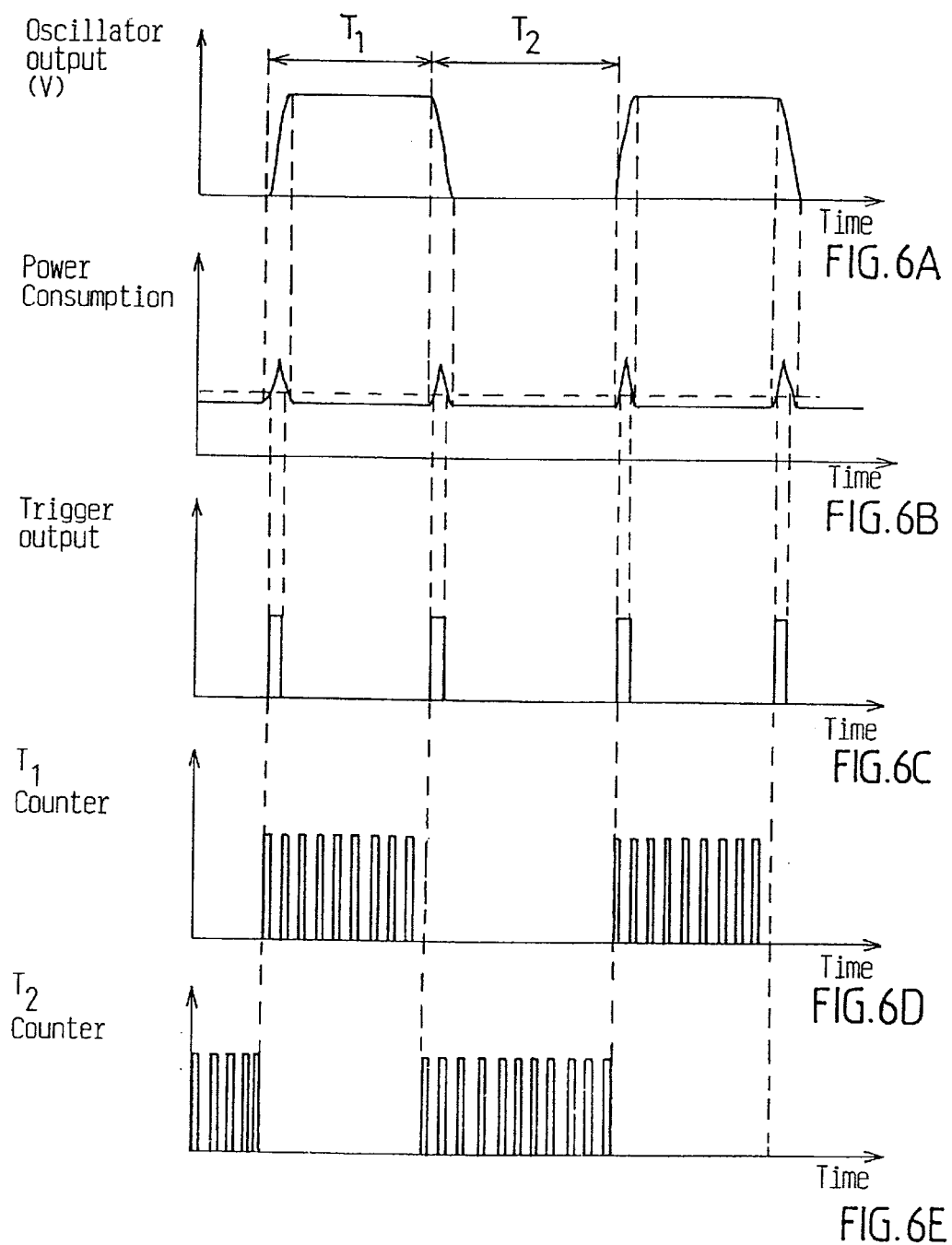
FIGS. 6A and 6B are interconnected time charts illustrating the decoding of a measure signal provided by a sensor unit arranged according to the invention.

FIG. 6A shows an oscillator output signal from sensor unit 303. The measuring conditions, i.e. the measured variable (or variables), determines the pulse width T1 and T2.

FIG. 6B shows the power consumption of sensor unit 303. The power consumption is essentially constant with superimposed peaks coinciding in time with the sensor oscillator's transition from "0" to "1", or vice versa.

FIG. 6C shows an output signal from Schmitt-trigger 307. The trigger threshold is shown as a horizontal dotted line in FIG. 6B.

FIG. 6D illustrates clock pulses from clock pulse generator 309 being calculated by micro processor 308 to determine the time interval T1.

FIG. 6E illustrates clock pulses from clock pulse generator 309 being calculated by micro processor 308 to determine the time interval T2.

Thus, by determining the time intervals coded by the sensor and its corresponding circuit, information on the measured physiological variable can be obtained via an electrical signal passing through the body tissue.

Figure 9:
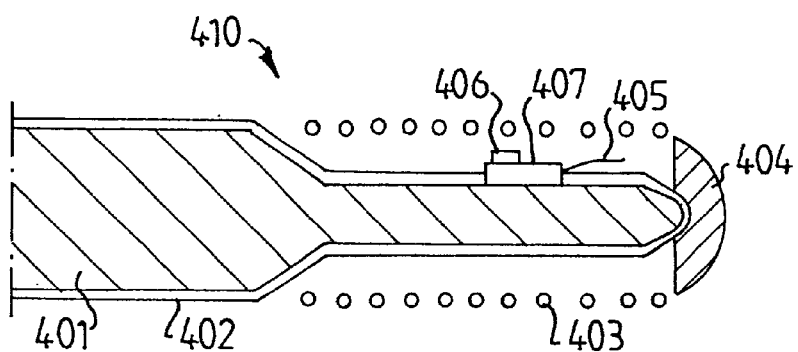
FIG. 9 shows an embodiment of the present invention including an acoustical sensor.

FIG. 9 shows an embodiment of the present invention including an acoustical sensor. As with previous embodiments, a guide wire 410 comprises a core wire 401 covered with an insulating layer 402. The distal end of the guide wire has a rounded tip 404. A coil 403 connected to element 405 acts as an output signal electrode according to the invention, similarly to what is previously described.

A piezo-ceramic plate 407, such as a PZT (lead zirconate-titanate) plate, is connected to the core wire and to output signal electrode 403. A micro-mechanical acoustic resonator 406 is attached to piezo-ceramic plate 407. The resonator should be selected such that its resonance frequency is dependent on the physiological variable to be measured.

Examples of useful micro-mechanical acoustic resonators are described in U.S. Pat. No. 5,188,983, "Polysilicon resonating beam transducers and methods of producing the same" to H Guckel et al.

Figure 10:
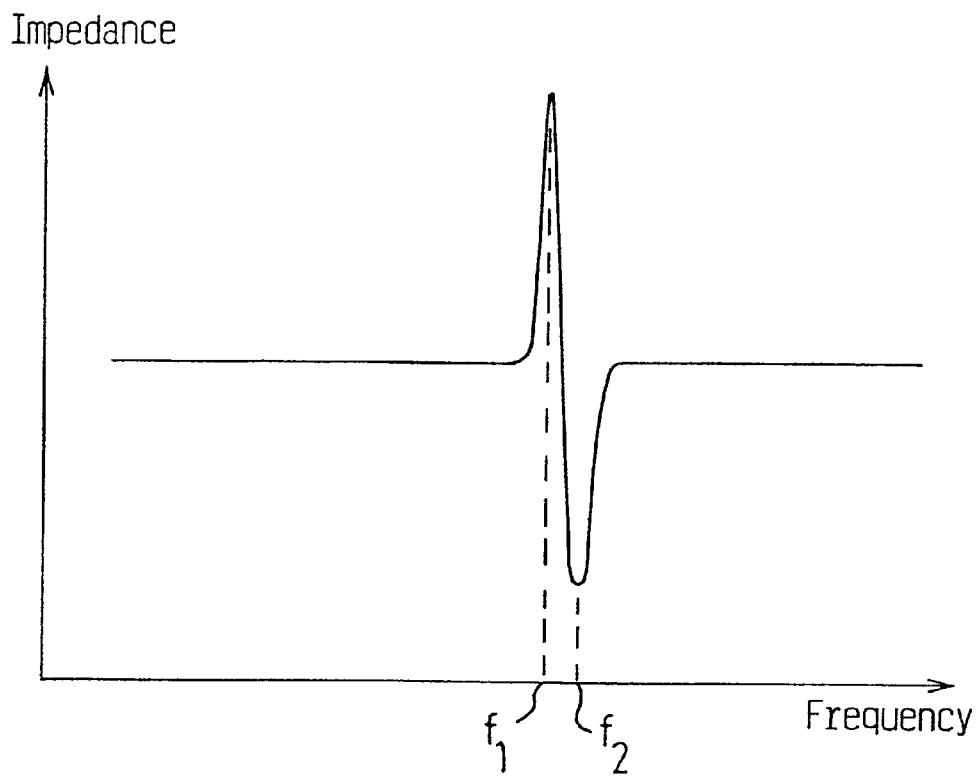
FIG. 10 is an impedance vs. frequency chart for an embodiment with an acoustic sensor.

When piezo-ceramic plate 407 is energised by alternating voltage provided via the body tissue, as described above, it responds with mechanical vibrations that are transferred to resonator 406. As illustrated in FIG. 10, at resonance frequencies f1 or f2 (corresponding to serial or parallel resonance), a peak and a valley point, respectively, appear in the electrical impedance. The electrical impedance is detectable by an external electronic unit, corresponding to the unit described above with reference to FIG. 5, and consequently the physiological variable sought for can be calculated.

Thus, the guide wire assembly and the communicating system according to the invention, for determining a physical parameter inside the body of a patient, enables the transfer of information regarding a physiological variable detected by a sensor inside the body using a single electrical wire provided in the guide wire. According to the invention, this is obtained by using tissue of the patient, such as the blood and the skin, to act as a conductor in co-operation with a guide wire according to the invention.

A guide wire assembly according to the present invention provides for very simple manufacturing, using few components. The circuitry of the sensor, with the associated internal body electrode, is easily connected to an exposed section of the core wire at the distal end of the guide wire using any suitable conventional method, such as soldering. No additional cables are called for, allowing the core wire to be connected to the electronic unit with any suitable connector means.

In addition, as is shown in the embodiments described above, the present invention allows a sensor guide wire design wherein the absence of conduits other than the core wire provides a suitable flexibility and symmetry to allow good maneuverability during positioning of the guide wire in a vessel.

Figure 7:
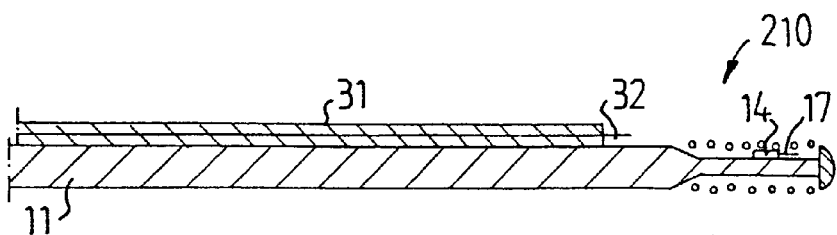
FIG. 7 is an illustration of a double wire embodiment of the present invention.

Another embodiment of the invention, herein called the double wire embodiment, is illustrated in the schematical illustration of FIG. 7. According to FIG. 7, guide wire 210 is similar to guide wire 10 shown in FIG. 1, including, for example, an insulated core wire 11. Guide wire 210 is additionally provided with a second insulated wire 31. At a distal portion, near the distal end of guide wire 210, the insulation is removed from second wire 31 to expose the conductor to form an electrode 32.

Figure 8:
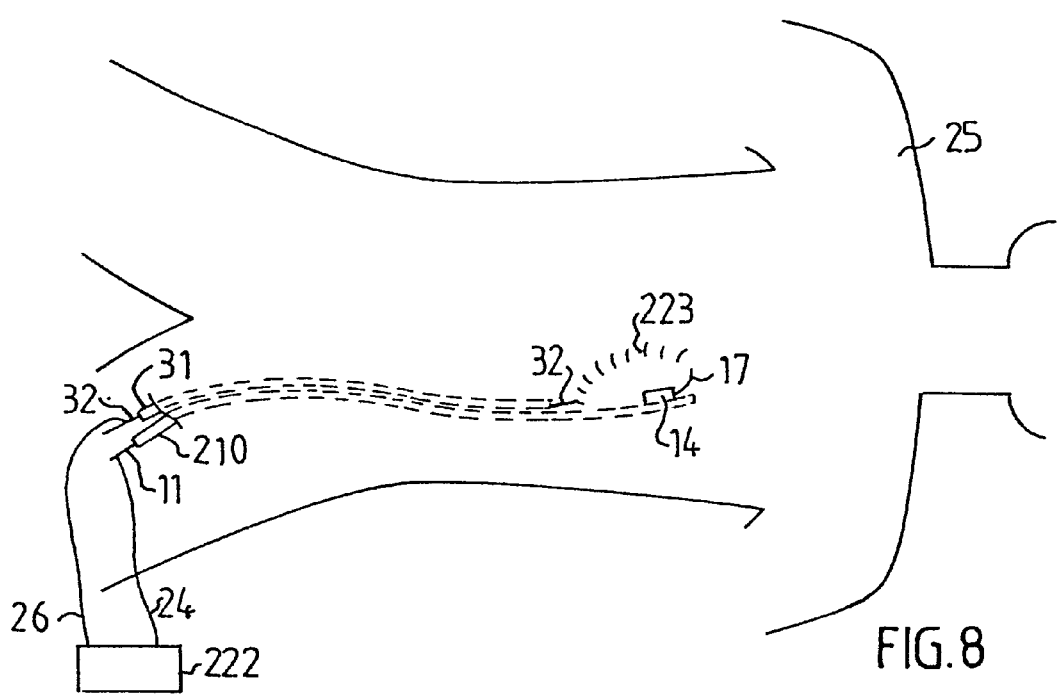
FIG. 8 is a schematic view illustrating the embodiment of FIG. 7 used on a patient.

When inserted into patient's body 25, as is shown in FIG. 8, core wire 11 of guide wire 210 is connected to an electronic unit 222, similar to electronic unit 22 of the first embodiment. Second electrical wire 31 is also connected to electronic unit 222. At the same time electrode end 32 of the second insulated wire is inserted in the body with the guide wire to contact the body fluids of the patient. In use, the electric circuit including core wire 11, sensor (and any additional electronic circuits) 14, output signal electrode 17, conductor 31 and its electrode end 32, connecting leads 24, 26, and electronic unit 222 is closed via body tissue 23, e.g., the blood, of the patient.

Thus, similarly to what has been explained for the previous embodiments, the electric circuit includes tissue of the patient's body. However, in the double wire embodiment no electricity is transferred through the skin of the patient and no electrode is applied on the skin of the patient. Instead, the electronic signals leaving output signal electrode 17 propagates through the surrounding blood to second electrical wire 31.

Thus, with the double wire embodiment it is not necessary to apply an electrode to the skin of the patient, although this is obtained to the cost of a more complicated and hard to manipulate guide wire.

Although it is necessary to connect the guide wire according to the second embodiment using two connectors, anyone of these connectors could be any suitable connector, such as a simple low-cost connector of crocodile type.

What is claimed is:

1. A system for the measurement of a physiological characteristic comprising the following:
    a first electrode adapted to be in electrical contact with body tissue at a first part of a body, wherein said first electrode is connected to a sensor for measuring a physiological characteristic;
    a second electrode adapted to be in electrical contact with body tissue at a second part of the body;
    an electrical circuit comprising the first electrode, the sensor, and the second electrode, wherein said electrical circuit is completed via body tissue; and
    a first electrical wire having a distal end for insertion into body tissue and a proximal end for connection to the electrical circuit;
    wherein the sensor is adapted to the distal end of the first electrical wire to allow said sensor to be inserted into body tissue; and
    wherein said system is adapted to transfer an electrical signal representing a physiological characteristic through said first and second electrodes via the body tissue.

2. The system of claim 1 wherein the first electrical wire is adapted for intravascular routing.

3. The system of claim 2 wherein the first electrical wire comprises a core wire extending through a guide wire.

4. The system of claim 1 wherein body tissue at the second part of the body comprises skin of the body.

5. The system of claim 1 wherein the second electrode comprises a second electrical wire having a distal end for insertion into body tissue and a proximal end for connection to the electrical circuit.

6. The system of claim 5 wherein the first electrode is adaptable to be in electrical contact with the second electrode via blood of the body.

7. The system of claim 3 wherein the second electrode is mounted on the guide wire and wherein the first electrode is in electrical contact with the second electrode via body tissue.

8. The system of claim 1 wherein the electrical circuit comprises an AC power source to power the sensor with an AC voltage.

9. The system of claim 8 wherein the AC voltage is within the range of 2–10V, and is of a frequency within the range of 100 kHz–1 MHz.

10. The system of claim 1 wherein the electrical circuit comprises a DC voltage supply.

11. A method for the measurement of a physiological characteristic comprising the following:
    placing a first electrode in electrical contact with body tissue at a first part of a body, wherein said first electrode is connected to a sensor for measuring a physiological characteristic;
    placing a second electrode in electrical contact with body tissue at a second part of the body;

completing, through body tissue, an electrical circuit comprising the first electrode, the sensor, and the second electrode; and registering a signal from the sensor wherein said signal represents the physiological characteristic;

wherein the step of placing a first electrode further comprises inserting, a first electrical wire into body tissue and connecting a proximal end of the first electrical wire to the electrical circuit and wherein the sensor is adapted to the distal end of the first electrical wire.

12. The method of claim 11 wherein the step of placing a first electrode comprises intravascularly routing the sensor until the sensor is in proximity to where the pysiological characteristic is to be measured.

13. The method of claim 12 wherein the step of placing a first electrode comprises routing the sensor a the first electrical wire and wherein the first electrical wire comprises a core wire extending through a guide wire.

14. The method of claim 11 wherein the step of placing a second electrode comprises electrically connecting the second electrode to the skin of the body.

15. The method of claim 11 wherein the step of placing a second electrode comprises inserting the second electrode into body tissue.

16. The method of claim 15 wherein the first electrode is in electrical contact with the second electrode via blood of the body.

17. The method of claim 13 wherein the second electrode is mounted on the guide wire and wherein the first electrode is in electrical contact with the second electrode via body tissue.

18. The method of claim 11 wherein the electrical circuit comprises an AC power source to power the sensor with an AC voltage.

19. The method of claim 18 wherein the AC voltage is within the range of 2–10 V, and is of a frequency within the range of 100 kHz–1 MHz.

20. The method of claim 11 wherein the electrical circuit comprises a DC voltage supply.

21. A system for the measurement of a physiological characteristic comprising the following:

a first electrode adapted to be in electrical contact with body tissue at a first part of a body;

a sensor for measuring a physiological characteristic, wherein said sensor is mounted on a guide wire and connected to said first electrode;

a second electrode adapted to be in electrical contact with body tissue at a second part of the body;

an electrical circuit comprising the first electrode, the sensor, and the second electrode, wherein said electrical circuit is completed via body tissue; and wherein said system is adapted to transfer an electrical signal representing a physiological characteristic through said first and second electrodes via the body tissue.

22. The system of claim 21, further comprising a coil disposed around a distal end of said guide wire, wherein said coil is connected to the sensor.

* * * * *